US006699679B2

(12) United States Patent
Chen et al.

(10) Patent No.: US 6,699,679 B2
(45) Date of Patent: Mar. 2, 2004

(54) **METHODS FOR RAPID IDENTIFICATION OF *BACILLUS CEREUS***

(75) Inventors: Chi Hua Chen, Hsinchu (TW); Tsung C. Chang, Tao Yuan Hsien (TW); Hwia C. Ding, Hsinchu (TW)

(73) Assignee: Food Industry Research and Development Institute, Taiwan (CN)

( * ) Notice: Subject to any disclaimer, the term of this patent is extended or adjusted under 35 U.S.C. 154(b) by 0 days.

(21) Appl. No.: 10/022,591

(22) Filed: Dec. 17, 2001

(65) Prior Publication Data

US 2002/0146752 A1 Oct. 10, 2002

(30) Foreign Application Priority Data

Jan. 31, 2001 (TW) ....................................... 90101886 A

(51) Int. Cl.$^7$ ............................................. G01N 33/554

(52) U.S. Cl. ........................ 435/7.32; 435/7.1; 435/7.2; 435/7.92; 435/34; 435/975

(58) Field of Search ........................ 435/975, 7.1, 7.32, 435/7.92, 7.2, 34; 530/387.1, 388.1; 424/130.1, 150.1, 164.1

(56) References Cited

U.S. PATENT DOCUMENTS 5,763,226 A * 6/1998 Wong et al.
6,284,517 B1 9/2001 Restaino .................. 435/252.4
2002/0082386 A1 6/2002 Mangold et al. ............ 530/350

FOREIGN PATENT DOCUMENTS

WO 8602363 4/1986
WO 9936081 7/1999

OTHER PUBLICATIONS

Koo et al. May 19–23, 1996. ASM Abstracts. New Orleans, USA. 96(O). p. 381.*

Nielsen et al. J.Biol. Chem. 1982. 257(8): 4490–4495.*

Harmon et al. 1992. Compendium of methods for the Microbiological Examination of foods. 3rd ed. American Public Health Association. Washington DC., pp. 593–604. reference not included. Cited on p. 1 of Applicants' specification.*

* cited by examiner

*Primary Examiner*—Jennifer E. Graser
(74) *Attorney, Agent, or Firm*—Ladas & Parry

(57) ABSTRACT

The present invention provides a method for rapid identification of *Bacillus Cereus* comprising utilizing an antibody specific to a certain surface antigen of *B. cereus*, and the kit for performing the method.

14 Claims, 2 Drawing Sheets

METHODS FOR RAPID IDENTIFICATION OF BACILLUS CEREUS

FIELD OF THE INVENTION

This invention relates to a method for rapid identification of *Bacillus cereus* and the kit thereof.

BACKGROUND OF THE INVENTION

*Bacillis cereus* is gram-positive, spore-forming, motile, aerobic rod which inhibits in soil and has been recognized as an opportunistic food poisoning pathogen. *Bacillis cereus* and the poison thereof usually result in the diarrheal syndrome and the emetic syndrome. Some food types that are preferentially contaminated with *B. cereus* are crude cereals, starchy foods, dairy products, meat, dehydrated foods, and spices.

Conventional procedures for the detection of *B. cereus* are based on morphologic observations, physiological and biological tests, such as plate count method and most probable number method. Harmon et al. utilized the hydrolysis of lecithin (egg yolk reaction) as a characteristic for isolation of suspect *B. cereus* on selection media such as mannitol-egg yolk-polymyxin (MYP) agar. However, it should take several days to complete the physiological and biological tests. (Harmon, S. M. et al., 1992, Compendium of methods for the Microbiological examination of foods. 3$^{rd}$ ed. American Public Health Association, Washington, D.C., pages 593–604) Schraft et al. developed polymerase chain reaction for detection of lecithin-hydrolyzing gene of *B. cereus*. Since most strains of the *B. cereus* group (i.e., *B. cereus*, *B. mycoides* and *B. thuringiensis*) possess lecithinase activity, the polymerase chain reaction method detects all species of the *B. cereus* group, but does not distinguish any single species. (Schraft, H. and M. W. Griffiths, 1995, Sepecific oligonucleotide primers for detection of lecithinase-positive Bacillus spp. by PCR. Appl. Environ. Microbiol. 61: 98–102). Thus, a rapid and specific method for identification of *B. cereus* is desired.

SUMMARY OF THE INVENTION

The objective of this invention relates to provide a method for rapid identification of *Bacillus cereus* in a sample comprising
(a) mixing an antibody or antisera specifically against the cell surface antigens of *B. cereus* with the sample, wherein the surface antigen is selected from the group of consisting of: surface antigens of *B. cereus* with molecular masses of 28.5, 26.5 and 20 kDa and the mixture thereof; and
(b) detecting the existence of *B. cereus* if the antibody-antigen binding reaction is positive.

Another objective of this invention is to provide a kit for rapid identification of *B. cereus*, which comprises a solution of antibody or antisera against the cell surface antigens of *B. cereus*, and the agents and apparatus required for detection of binding reaction between the said antibody or antisera and the bacteria antigen in a test sample; wherein the antigen is selected by at least one from the group consisting of: surface antigen of *B. cereus* with molecular masses of 28.5, 26.5 and 20 kDa and the mixture thereof.

BRIEF DESCRIPTION OF THE DRAWINGS

FIG. 1A is the SDS-PAGE of cell surface antigens extracted with 1% sodium dodecyl sulfate. Left lane represents molecular weight markers. Lanes 1 through 6 represent *B. cereus* CCRC 10603, 11026, 15840, 15843, 15846 and 13481, respectively. FIG. 1B is the SDS-PAGE of cell surface antigens extracted with 1% SDS from Bacillus spp. Left lane represents molecular weight markers. Lanes 1 and 2 represent *B. cereus* CCRC 10603 and 11026, respectively. Lane 3 represents *B. mycoides* CCRC 12022. Lane 4, *B. licheniformis* CCRC 11556; Lane 5, *B. subtilis* CCRC 10029; and lane 6, *B. megaterium* CCRC 10608.

DETAILED DESCRIPTION OF THE INVENTION

Figure 1:
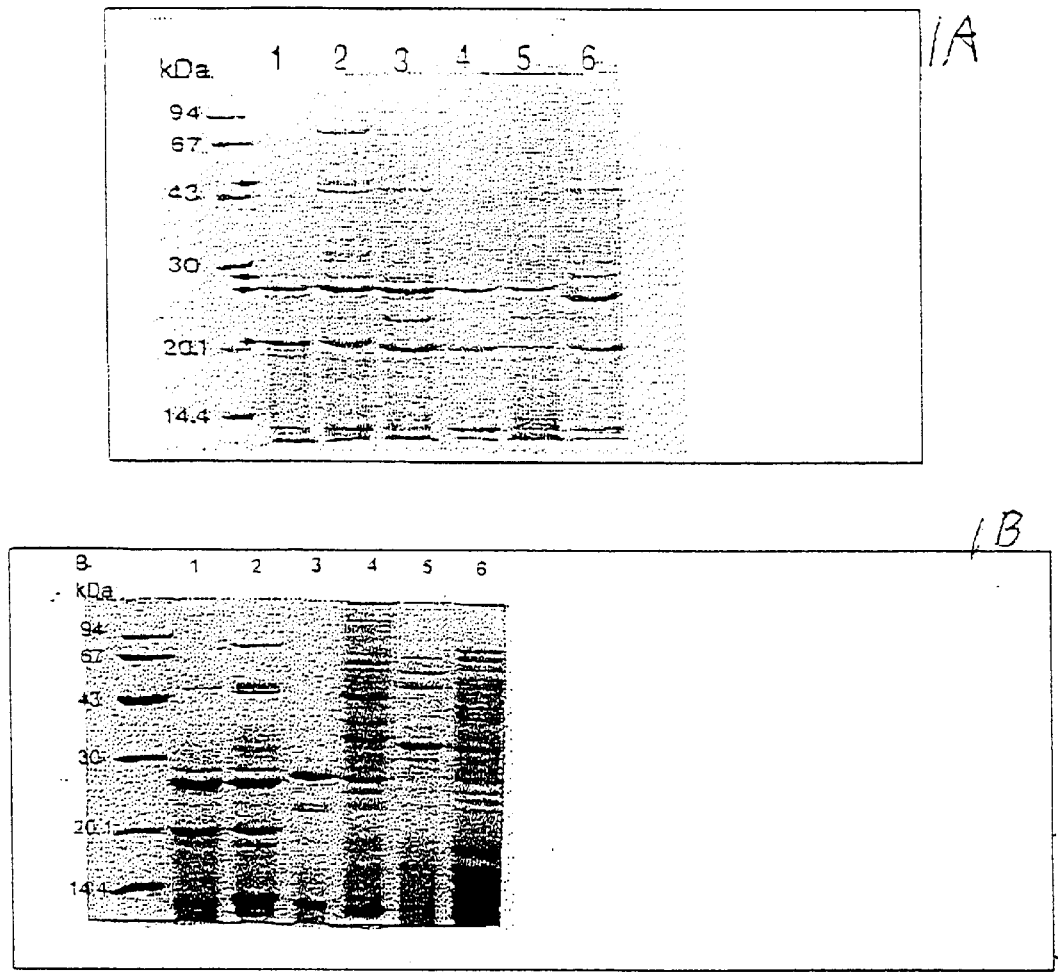
FIG. 1 demonstrates the SDS-polyacryl amide gel electrophoresis (SDS-PAGE) of *Bacillus cereus* and Bacillus spp.
Figure 2:
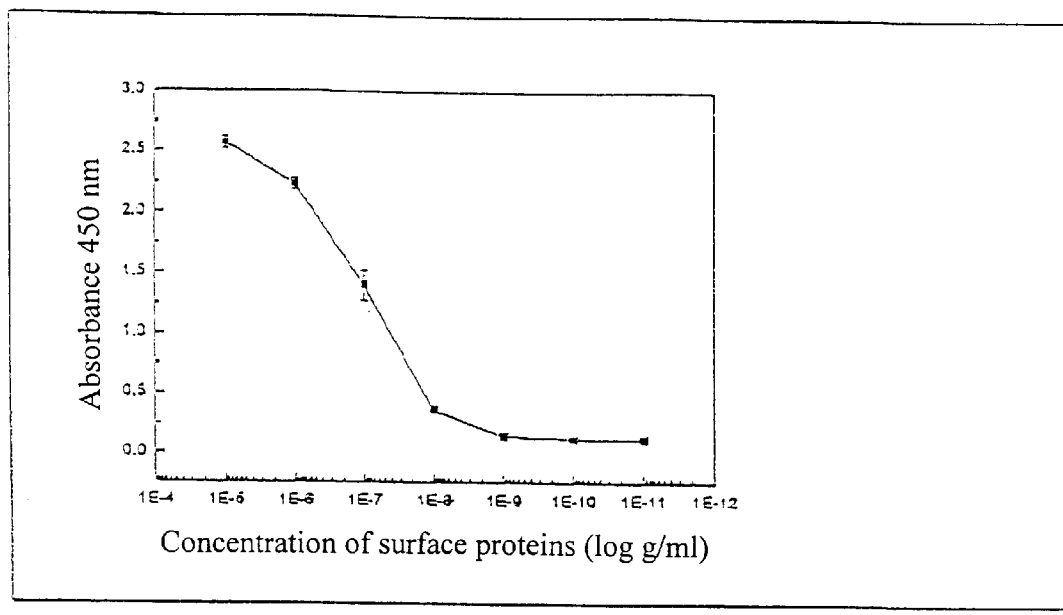
FIG. 2 demonstrates a dose-response curve between the concentration of total cell surface antigens of *B. cereus* CCRC 10603 and $A_{450}$ as determined by ELISA using the antibodies against the 28.5 kDa antigen.

This invention is the first one by immunological methods for the identification of *B. cereus*, which is characterized by the binding of special surface antigen of *B. cereus* and specific antibody to achieve the purpose of rapid identification. According to the invention, the identification method is very simple, fast, highly sensitive and specific.

The objective of this invention relates to providing a method for rapid identification of *Bacillus cereus* in a sample comprising
(a) mixing an antibody or antisera specifically against the cell surface antigen of *B. cereus* with the sample, wherein the surface antigen is selected from the group of consisting of: surface antigen of *B. cereus* with molecular masses of 28.5, 26.5 and 20 Kda and the mixture thereof; and
(b) detecting the existence of *B. cereus* if produce antibody-antigen binding reaction.

According to the invention, the term "antibody" is defined as any immunoglobulin against a specific antigen produced from animals. The term "antisera" refers to the animal serum rich in specific antibodies, obtained after immunization. In general, antibodies are produced by immunizing animals (such as rabbits, goats and mice) with an antigen which is emulsified with an adjuvant. The preparation of antibodies or antisera is well known to the persons skilled in the art. The surface protein of *B. cereus* used for production of an antibody from immunized animals is purified through SDS-PAGE. Although the protein is denatured, the antibody produced therefrom is able to recognize the surface protein of *B. cereus*. The antibody can react with some antigenic epitopes of the native protein due to the polyclonal property.

The surface antigen of *B. cereus* used in the invention includes the surface antigens with molecular masses of 28.5 kDa, 36.5 kDa or 20 kDa or the mixture thereof. The antigen is preferably with molecular masses of 28.5 kDa and 20 kDa. More preferably, the molecular weight of the antigen is 28.5 kDa. The relevant preparation and purification of the surface antigen of the invention can be carried out by any conventional methods or techniques, for example, as described in the examples.

According to this invention, the antibodies against surface antigens of *B. cereus* possess high titers. Preferably, the titer is $1 \times 10^5 – 1 \times 10^8$. More preferably, it is $1 \times 10^6 – 1 \times 10^7$. The 28.5 kDa antigen has a stronger antigenicity than 26.5 kDa antigen and 20 kDa antigen.

According to this invention, any suitable method for detection of an antibody-antigen binding reaction can be used for detection of the binding of surface antigen of *B.* cereus and antibody of the invention. A preferred method is enzyme-linked immunosorbent assay (ELISA) or colony blot immunoassay.

In one preferred embodiment of the invention, the antigen-antibody reaction is combined with mannitol-egg yolk-polymyxin (MYP) selective agar.

Another objective of this invention is to provide a kit for rapid identification of B. cereus, which comprises an antibody or antisera against the cell surface antigens of B. cereus, and the agents and apparatus required for detection of binding reaction between the said antibody or antisera and the bacteria antigen in the test sample; wherein the antigen is selected by at least one from the group of consisting of: surface antigen of B. cereus with molecular masses of 28.5, 26.5 and 20 kDa and the mixture thereof. The agents and apparatus can be prepared or produced by the persons skilled in the art according to conventional technology and knowledge.

This invention provides a sensitive and specific method for rapid identification of B. cereus and the kit thereof, which completes the identification of B. cereus in short time with minimum labor and expense.

EXAMPLES

Example 1

Identification of B. cereus

Bacteria and Culture Conditions

A total of 165 bacterial strains (Table 1) were tested in this study including 38 strains of B. cereus, 79 strains of other Bacillus spp., and 48 non-Bacillus strains. Most cultures were obtained from the Culture Collection and Research Center (CCRC, Food Industry Research and Development Institute, Hsinchu, Taiwan). Bacillus anthracis ATCC 8705 and ATCC 14578 were obtained from the American Type Culture Collection (Rockville, Md.). Cultures of Bacillus spp. were maintained on nutrient agar, whereas non-Bacillus bacteria were maintained on tryptic soy agar. For ELISA, Bacillus spp. were grown at 30° C. on MYP agar or nutrient agar, and other bacteria were grown at 37° C. on tryptic soy agar for 20 to 24 hours before analysis.

TABLE 1

| Microorganism | CCRC No. | Total | ELISA-positive | ELISA-negative |
|---|---|---|---|---|
| Bacillus cereus | (CCRC no. is not specified for each individual strain) | 38 | 38 | 0 |
| B. alvei | 11840, 11842, 11220, 11728, 11906, 11970 | 6 | 0 | 6 |
| B. anthracis[a] | 8705, 14578 | 2 | 2 | 0 |
| B. apiarius | 11830 | 1 | 0 | 1 |
| B. badius | 11699, 11909 | 2 | 0 | 2 |
| B. brevis | 10600, 11717, 11047, 11841, 11912 | 5 | 0 | 5 |
| B. circulans | 13842, 13847, 10605, 11027 | 4 | 0 | 4 |
| B. coagulans | 10606, 10272, 11592, 12147, 12210, 11700 | 6 | 0 | 6 |
| B. firmus | 11729, 11730 | 2 | 0 | 2 |
| B. insolitus | 11737 | 1 | 0 | 1 |
| B. larvae | 14187 | 1 | 0 | 1 |
| B. laterosporus | 10607, 11951 | 2 | 0 | 2 |
| B. lentus | 11735, 12021 | 2 | 0 | 2 |
| B. licheniformis | 11556, 12826, 11702 | 3 | 0 | 3 |
| B. macerans | 12025, 13021, 14680 | 3 | 0 | 3 |

TABLE 1-continued

| Microorganism | CCRC No. | Total | ELISA-positive | ELISA-negative |
|---|---|---|---|---|
| B. maroccanus | 14649 | 1 | 0 | 1 |
| B. megaterium | 10608, 14706, 11962, 11965 | 4 | 0 | 4 |
| B. mycoides | 10604, 11968, 12022, 11716 | 4 | 4 | 0 |
| B. pabuli | 15857 | 1 | 0 | 1 |
| B. pantothenticus | 14681 | 1 | 0 | 1 |
| B. polymyxa | 14352, 12011, 12012 | 3 | 0 | 3 |
| B. popilliae | 14650 | 1 | 0 | |
| B. pulvifaciens | 15859 | 1 | 0 | 1 |
| B. pumilus | 14688, 14700 | 2 | 0 | 2 |
| B. racemilacticus | 12807 | 1 | 0 | 1 |
| B. sphaericus | 14354, 12825, 11066, 12006, 14702, 14703 | 6 | 0 | 6 |
| B. stearothermophilus | 10610, 11092 | 2 | 0 | 2 |
| B. subtilis | 10029, 12815 | 2 | 0 | 2 |
| B. thuringiensis | 14380, 14381, 14683, 15853, 15854, 15855, 15856 | 7 | 7 | 0 |
| B. thuringiensis subsp. israelensis | 15860 | 1 | 1 | 0 |
| Bacillus spp. | 12276, 14642 | 2 | 0 | 2 |
| Corynebacterium ammoniagenes | 10367, 12469 | 2 | 0 | 2 |
| C. glutamicus | 10488 | 1 | 0 | 1 |
| C. glutamicum | 11384 | 1 | 0 | 1 |
| Eschericia coli | 10675, 10314, 10316, 10324, 14824 | 5 | 0 | 5 |
| Enterobacter cloacae | 10370, 10401, 11507 | 3 | 0 | 3 |
| Methylobacterium extorquens | 11048, 12234 | 2 | 0 | 2 |
| Microbacterium ammoniaphilum | 11670, 12505 | 2 | 0 | 2 |
| Micrococcus luteus | 11271, 15275, 15276 | 3 | 0 | 3 |
| M. pyogenes | 11274, 11275 | 2 | 0 | 2 |
| M. varians | 15216, 15217 | 2 | 0 | 2 |
| Proteus mirabilis | 10725, 10726 | 2 | 0 | 2 |
| Pseudomonas aeruginosa | 10944 | 1 | 0 | 1 |
| Rhodococcus equi | 11367, 11368 | 2 | 0 | 2 |
| Salmonella Chester | 15468 | 1 | 0 | 1 |
| Salmonella Etterbeek | 15455 | 1 | 0 | 1 |
| Salmonella Simsbury | 15580 | 1 | 0 | 1 |
| Salmonella Tennessee | 15581 | 1 | 0 | 1 |
| Shigella boydii | 10771 | 1 | 0 | 1 |
| S. sonnei | 10773, 10774 | 2 | 0 | 2 |
| Sphingomonas paucimobilis | 13954, 13955 | 2 | 0 | 2 |
| Sporosarcina urea | 10766 | 1 | 0 | 1 |
| Staphylococcus aureus | 11551, 14941, 14943, 14944 | 4 | 1 | 3 |
| S. epidermidis | 15245, 15246, 15247 | 3 | 0 | 3 |
| Streptococcus agalactiae | 10787 | 1 | 0 | 1 |
| S. mutans | 10793 | 1 | 0 | 1 |
| S. salivarius | 12257 | 1 | 0 | 1 |

[a]The two strains of B. anthracis were from ATCC.

Preparation of Cell Surface Antigens

The purification method was a modification of that described by Bhunia et al. (Bhunia et al., Infect. Immun. 59:3176–3184). B. cereus CCRC 10603 was grown on nutrient agar plates at 30° C. for 18 hours. Two milliliters of 70 mM phosphate buffer (pH 6.8) was added to each plate to harvest the bacteria. The cells were washed with the same phosphate buffer and centrifuged at 3,000×g for 15 min. The cell surface antigens were extracted with 2 ml of 70 mM phosphate buffer (pH 6.8) containing 1% sodium dodecyl sulfate (SDS) and 0.5% β-mercaptoethanol. After incubation at 70° C. for 20 min, the cell pellet was removed by centrifugation (10,000×g for 10 min), and the supernatant containing the SDS-extracted cell surface antigens was dialyzed for 18 to 24 hours. Cell-surface antigens of other strains were extracted with SDS in a similar manner.

Purification of Cell Surface Antigens

The extracted cell surface antigens were analyzed with SDS-polyacrylamide gel electorphoresis (SDS-PAGE). After electropohoresis, gels were stained with Coomassie brilliant blue. FIG. 1 demonstrates SDS-PAGE of strains B. cereus and Bacillus spp. as control. As indicated in FIG. 1A, the protein patterns of most strains of B. cereus had two major common bands with molecular masses of 26.5 and 20 kDa and a minor band with a molecular mass of 28.5 kDa (FIG. 1A, indicated by arrow heads). FIG. 2B indicates that there were more variations in the band patterns of other Bacillus spp.

Preparation of Antibodies

The protein bands corresponding to molecular masses of 28.5, 26.5 and 20 kDa were separately cut into small pieces, ground to fine particles with a hand homogenizer, and emulsified with incomplete Freund's adjuvant (Dicfo Laboratories, Detroit, Mich., USA). Two milliliters of the emulsified antigen were used to immunize New Zealand white rabbits (2.5 Kg in weight). Each rabbit was boosted four times at 3-week intervals. Ten days after the final injection, blood was collected from the rabbits' ears. The antisera were decomplemented by heating at 56° C. for 30 min, and titers of the decomplemented antisera were determined by ELISA. Microtiter plates (Nunc, Denmark) were coated with SDS-extracted total cell surface antigens (10 $\mu$g/ml), and after the addition of serial 10-fold diluted antisera, protein A horseradish peroxidase (HRP) conjugate was used as the signal producer. The titers of the antisera against each of the 28.5 kDa, 26.5 kDa and 20 kDa antigens were around $1\times10^6$ to $1\times10^7$ as determined by ELISA. Although the abundance of the 28.5 kDa antigen was relatively small (FIG. 1A), the titers of antibodies against this protein were comparable to those obtained against the 26.5 kDa and 20 kDa proteins. It was possible that the 28.5 kDa antigen had a stronger antigenicity than the other two antigens with molecular masses of 26.5 kDa and 20 kDa.

Purification of Antibodies and Preparation of Antibody-enzyme Conjugate

The immunoglobulin G (IgG) fraction of the antisera against each of the 28.5, 26.5 and 20 kDa antigens was purified by ammonium sulfate precipitation followed by diethylaminoethyl ion-exchange chromatography (Chen et al., J. Food Prot. 58: 873–878). Specific antibodies were further purified by affinity chromatography, using the SDS-extracted total cell surface antigens of *B. cereus* CCRC 10603 as ligands coupled to cyanogens bromide-activated Sepharose 4B gel (Amersham Pharmacia Biotech, Uppsala, Sweden). The affinity-purified antibodies against each antigen were conjugated with HRP (Boehringer GmbH, Mannheim, Germany) using the sodium peroxidase oxidation protocol (Hudson et al., 1989, Practical Immunology, $3^{rd}$ ed., Blackwell Scientific Publication, London).

Identification of *B. cereus* by ELISA

The antibodies against each of the 28.5, 26.5 and 20 kDa antigens were used as capture and detection antibodies. Wells of microtiter plates were coated with 0.1 ml of affinity-purified antibodies (10 $\mu$g/ml) at 37° C. for 2 hours. The plates were washed with PBS containing 0.05% Tween 20 (PBST), blocked overnight with 1% bovine serum albumin (BSA) at 4° C., and washed again with PBST. One colony grown on MYP agar or tryptic soy agar was suspended in 0.2 ml of PBS containing 0.1% Teepol (primary alkyl [$C_9$–$C_{13}$] sodium sulfates; Sigma, St. Louis, Mo.). The suspension was heated in a boiling water bath for 5 min and centrifuged (5,000×g for 10 min) to remove insoluble cells and debris. The resulting supernatant was diluted 1:1 with 2% BSA, and 0.1 ml of the diluted sample was added to each well of the microtiter plates. The plates were incubated at 37° C. for 1 hour and washed with PBST, and 0.1 ml of HRP-antibody conjugate diluted 1:10,000 in 1% BSA was added to each well. After 1-hour incubation at 37° C. and PBST washing, 0.1 ml of HRP substrate (3,3',5,5'-tetramethylbenzidine and $H_2O_2$; Kirkegarrd and Perry Laboratories, Gaithersburg, Md.) was added to each well. The reaction was stopped by the addition of 0.1 ml of 1 M $H_3PO_4$ to each well, and absorbance at 450 nm ($A_{450}$) was recorded with an ELISA reader. A reading of $A_{450}$ higher than that of the negative control plus three standard deviations was considered a positive reaction. PBS was used as a negative control. FIG. 2 shows a dose-response curve between the concentration of total cell surface antigens of *B. cereus* CCRC 10603 and the ELISA signal. According to the invention, the sensitivity of the assay for the detection of total cell surface antigens of *B. cereus* is 10 ng/ml.

Table 2 shows that the antibodies against the 28.5, 26.5 and 20 kDa antigens are used to test *B. cereus* CCRC 10446, 10927 and 11026. All the antibodies could effectively detect their relevant antigens. The ELISA signals produced by the antibodies against the 28.5 and 20 kDa antigens were stronger than those produced by the antibodies against the 26.5 kDa antigen.

The ELISA results of individual species tested with the antibodies against the 28.5 kDa antigen are shown in Table 1. All 38 strains of *B. cereus* produced positive reactions. Most of the 127 strains of non-*B. cereus* bacteria produced negative reactions. However, all strains belonging to the *B. cereus* group (i.e., *B. anthracis, B. mycoides* and *B. thuringiensis*) produced false-positive results. Similar results were obtained by using antibodies against the 20 kDa antigen to test the bacteria.

Identification of *B. cereus* by Colony Blot Immunoassay

The colonies of *B. cereus* on NA plates were transferred and dotted to a paper membrane prior to being rinsed with PBS. The membrane with dotted colonies was placed in an oven for 10 min for drying and irradiated by UV light (1.2 J/cm×0.1 min). The membrane was incubated with 1:2000 diluted antibody-enzyme conjugate solution and gently agitated for 60 min at room temperature. The membrane was rinsed in PBST for 5 min three times. Finally, the membrane was rinsed with PBS and stained in 4-CN (4-chloro-1-naphthol) color development solution for about 45 min and stopped the reaction by washing the membrane with water.

A total of 62 strains of *B. cereus* were tested; 61 strains produced positive reactions and 1 of them produced negative reactions. Thirty-six of the total 38 non-Bacillus spp. (19 species) produced negative reactions. The results described above indicate that the identification method of the invention is accurate and rapid for *B. cereus* identification.

TABLE 2

| | ELISA signal[a] (A450) using antibodies against antigen | | |
|---|---|---|---|
| Microorganism | 28.5 KDa antigen | 26.5 KDa antigen | 20 KDa antigen |
| *B. cereus* CCRC 10446 | 1.64 ± 0.03 | 1.14 ± 0.03 | 1.45 ± 0.02 |

TABLE 2-continued

| Microorganism | ELISA signal[a] (A450) using antibodies against antigen | | |
|---|---|---|---|
| | 28.5 KDa antigen | 26.5 KDa antigen | 20 KDa antigen |
| B. cereus CCRC 10927 | 0.67 ± 0.04 | 0.33 ± 0.01 | 0.43 ± 0.03 |
| B. cereus CCRC 11026 | 1.48 ± 0.07 | 1.17 ± 0.01 | 1.34 ± 0.00 |
| Negative control | 0.17 ± 0.001 | 0.11 ± 0.01 | 0.15 ± 0.01 |

[a]Mean ± SD of duplicate

Example 2

Detection of B. cereus in Foods

A total of 15 food samples, encompassing rice, beans, pudding, instant infant formula, pepper spice and ice cream were purchased from local supermarkets. The aerobic plate count of these samples was determined (Maturin et al., 1995, In Bacteriological Analytical Manual. 8th ed. Association of Official Analytical Chemists International, Arlington, Vir.). Serial 10-fold dilutions of the homogenized food samples were analyzed for B. cereus by inoculating three-tube MPN series in trypticase soy-polymyxin (TSP) broth. After selective enrichment, tubes that showed dense growth were subcultured onto separate MYP agar plates. One or more suspect colonies on each MYP agar plate were analyzed by ELISA for B. cereus identification; these colonies were also subcultured on nutrient agar slants followed by species identification with the conventional procedures.

Among the 15 food samples analyzed, B. cereus was detected in 11 samples by ELISA (see Table 3). However, only 10 samples were found to contain B. cereus as determined by the conventional method. The false-positive sample obtained by ELISA was mung bean, in which B. thruingiensis was isolated. Some strains of B. thuringiensis possess an interotoxin-like gene similar to that of B. cereus (Asano et al., 1997, Appl. Environ. Microbiol. 63:1054–1075). In addition, Carlson et al. strongly proposed that B. cereus and B. thuringiensis should be regarded as a single species (Carlson et al., Appl. Environ. Microbiol. 60: 1719–1725). The test results mentioned above exhibit relative accuracy of the method according to this invention for identification of B. cereus, which is useful for rapid identification of B. cereus.

TABLE 3

| Food | Aerobic plate count (CFU/g) | B. cereus (MPN/g) determined by: | |
|---|---|---|---|
| | | Conventional method | ELISA |
| Millet | $1.2 \times 10^3$ | 3.6 | 3.6 |
| Oat | $4.8 \times 10^2$ | NDb | ND |
| Rice | $4.3 \times 10^3$ | 9.1 | 9.1 |
| Waxy rice | $2.1 \times 10^3$ | 3.6 | 3.6 |
| Black soybean | $4.5 \times 10^3$ | 9.1 | 9.1 |
| Butter bean | $1.5 \times 10^3$ | 93 | 93 |
| Mung bean | $2.9 \times 10^3$ | ND | 3.6c |
| Kidney bean | $1.2 \times 10^3$ | 3.6 | 9.1d |
| Adzuki bean | $8.8 \times 10^3$ | 15 | 15 |
| Soybean | $2.1 \times 10^3$ | 23 | 93c |
| Spice | $4.9 \times 10^5$ | 3 | 3 |
| Ice cream | $1 \times 10^2$ | 23 | 23 |
| Instant infant formula | ND | ND | ND |
| Oak flake | $2.0 \times 10^2$ | ND | ND |
| Pudding | ND | ND | ND |

The examples described above are offered by way of illustration of the method for rapid identification of B. cereus and the kit thereof claimed in this subject application and not by way of limitation.

What is claimed is:

1. A kit for rapid identification for B. cereus comprising isolated antibodies against at least one cell surface antigen of B. cereus, and reagents and apparatus for detection of antibody-antigen binding reaction in a test sample; wherein the at least one antigen is selected from the group consisting of: surface antigens of B. cereus with molecular masses of 28.5, 26.5 and 20 Kda and a mixture thereof.

2. The kit according to claim 1, wherein the at least one antigen has a molecular mass of 28.5 kDa or 20 kDa.

3. The kit according to claim 2, wherein the at least one antigen has a molecular mass of 28.5 kDa.

4. The kit according to claim 1, wherein the reagents are combinable with MYP selective agar for rapid identification of B. cereus.

5. The kit according to claim 1, wherein the reagents and apparatus are adapted for use with an enzyme-linked immunosorbent assay (ELISA).

6. The kit according to claim 1 wherein the reagents and apparatus comprise means for carrying out colony blot immunassay.

7. The kit according to claim 1, wherein the isolated antibodies do not cross react with B. licheniformis strains having CCRC numbers 11556, 12826 and 11702.

8. A method for rapid identification of Bacillus cereus in a sample comprising:

(a) providing the kit of claim 7 and mixing the isolated antibodies with the sample, and (b) detecting whether there is an antibody-antigen binding reaction in the sample so as to ascertain the presence of B. cereus if the antibody-antigen binding reaction is positive.

9. The method according to claim 8, wherein the at least one antigen has a molecular mass of 28.5 kDa or 20 kDa.

10. The method according to claim 8, wherein the at least one antigen has a molecular mass of 28.5 kDa.

11. The method according to claim 8 wherein the reagents are combined with MYP selective agar for rapid identification of B. cereus.

12. The method according to claim 8, wherein the binding reaction is determined by enzyme-linked immunosorbent assay (ELISA).

13. The method according to claim 8, wherein the binding reaction is determined by colony blot immuoassay.

14. The method according to claim 8, wherein the isolated antibodies do not cross react with B. licheniformis strains having CCRC numbers 11556, 12826 and 11702.

* * * * *